United States Patent [19]

Staiger et al.

[11] Patent Number: 5,011,962
[45] Date of Patent: Apr. 30, 1991

[54] PROCESS FOR PREPARING ORGANOSILOXANES

[75] Inventors: Gerhard Staiger, Altölling; Johann Müller; Walter Doskocil, both of Burghausen, all of Fed. Rep. of Germany

[73] Assignee: Wacker-Chemie GmbH, Munich, Fed. Rep. of Germany

[21] Appl. No.: 530,380

[22] Filed: May 30, 1990

[30] Foreign Application Priority Data

Jun. 5, 1989 [DE] Fed. Rep. of Germany ....... 3918337

[51] Int. Cl.$^5$ .................... C07F 7/08; C07F 7/10
[52] U.S. Cl. .................... 556/453; 556/415; 556/427; 556/440; 556/449; 556/451; 556/452; 556/456; 556/459
[58] Field of Search ............... 556/451, 452, 415, 453, 556/454, 456, 449, 427, 440; 549/215

[56] References Cited

U.S. PATENT DOCUMENTS 3,839,388 10/1974 Kitzsche et al. ............... 556/453 X
4,053,494 10/1977 Burkhardt ............... 556/456 X
4,727,172 2/1988 Yamamoto et al. ............. 556/453 X Primary Examiner—Paul F. Shaver

[57] ABSTRACT

Organosiloxanes (1) of the general formula $$R^1{}_{4-n}Si(OSiR_3)_n,$$

in which R is the same or different and represents a hydrogen atom or a monovalent hydrocarbon radical having from 1 to 18 carbon atom(s) per radical or a substituted monovalent hydrocarbon radical having from 1 to 18 carbon atom(s) per radical, $R^1$ represents R or a chlorine atom, and n is 3 or 4, are prepared by reacting organodisiloxanes (2) of the general formula $$(R_3Si)_2O,$$

with chlorosilanes (3) of the general formula $$R_{4-n}SiCl_n,$$

in which R and n are the same as above, in the presence of phosphonitrile chlorides (4) and cocatalysts (5), in which the cocatalysts (5) are used concomitantly with the phosphonitrile chlorides (4) and are selected from the group consisting of amides of the general formula $$X-C(O)-R^2,$$

in which $R^2$ is the same or different and represents a hydrogen atom or a monovalent hydrocarbon radical having from 1 to 8 carbon atom(s) per radical or a substituted monovalent hydrocarbon radical having from 1 to 8 carbon atom(s) per radical, and X reresents a radical of the formula $R^2{}_2N-$ or

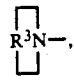

where $R^2$ is the same as above, $R^3$ represents a divalent hydrocarbon radical having from 5 to 7 carbon atoms per radical, urea or urea derivatives of the general formula $$X-C(O)-X,$$

where X is the same as above and cyanuric acid.

9 Claims, No Drawings

PROCESS FOR PREPARING ORGANOSILOXANES

The present invention relates to a process for preparing organopolysiloxanes and more particularly to a process for preparing organosiloxanes of the general formula $$R_{4-n}^1Si(OSiR_3)_n,$$

in which R is the same or different and represents a hydrogen atom or a monovalent hydrocarbon radical having from 1 to 18 carbon atom(s) and a substituted monovalent hydrocarbon radical having from 1 to 18 carbon atoms(s) per radical, $R^1$ represents R or a chlorine atom, and n is 3 or 4,

BACKGROUND OF THE INVENTION

Organohalosilicon compounds have been prepared by reacting halosilicon compounds with organosiloxanes containing no Si-bonded halogen, in the presence of phosphonitrile chlorides. (See GB-A 1,195,761 - published June 24, 1970, Wacker-Chemie GmbH). Also, the cleavage of organodisiloxanes using chlorosilanes in the presence of $FeCl_3$ and hydrogen chloride as catalyst is described in EP-B 115,772. (Published Feb. 15, 1989 H. J. Kötzsch et al., Hüls Troisdorf AG).

It is an object of the present invention to provide a process for preparing organosiloxanes. Another object of the present invention is to provide a process for preparing organopolysiloxanes by reacting organodisiloxanes with chlorosilanes in the presence of phosphonitrile chlorides, in which the organosiloxanes are obtained selectively and in higher yields than was possible heretofore. A further object of the present invention is to provide a catalyst system which does not promote removal of organic radicals from the silicon atoms and in which it is also possible to use organosilicon compounds which contain Si-bonded hydrogen or Si-bonded organofunctional groups.

SUMMARY OF THE INVENTION

The foregoing objects and others which will become apparent from the following description are accomplished in accordance with this invention, generally speaking, by providing a process for preparing organosiloxanes (1) of the general formula $$R_{4-n}^1Si(OSiR_3)_n,$$

in which R is the same or different and represents a hydrogen atom or a monovalent hydrocarbon radical having from 1 to 18 carbon atom(s) or a substituted monovalent hydrocarbon radical having from 1 to 18 carbon atom(s) per radical, $R^1$ represents R or a chlorine atom, and n is 3 or 4, which comprises reacting organodisiloxanes (2) of the general formula $$(R_3Si)_2O,$$

with chlorosilanes (3) of the general formula $$R_{4-n}SiCl_n,$$

in which R and n are the same as above, in the presence of phosphonitrile chlorides (4) as catalysts and cocatalysts (5) which are used concomitantly with the phosphonitrile chlorides (4) in which the cocatalysts (5) are selected from the group consisting of amides of the general formula $$X-C(O)-R^2,$$

in which $R^2$ is the same or different and represents a hydrogen atom or a monovalent hydrocarbon radical having from 1 to 8 carbon atoms or a substituted hydrocarbon radical having from 1 to 8 carbon atom(s) per radical, and X represents a radical of the formula $R^2{}_2N$—or

where $R^2$ is the same as above and $R^3$ represents a divalent hydrocarbon radical having from 5 to 7 carbon atoms per radical, urea or urea derivatives of the general formula $$X-C(O)-X,$$

where X is the same as above and cyanuric acid.

DESCRIPTION OF THE INVENTION

In the above formulas R is selected from the group consisting of a hydrogen atom, a monovalent hydrocarbon radical having from 1 to 18 carbon atoms per radical and a substituted monovalent hydrocarbon radical having from 1 to 18 carbon atoms per radical.

Examples of radicals represented by R are alkyl radicals, such as the methyl, ethyl, n-propyl, isopropyl, 1-n-butyl, 2-n-butyl, isobutyl, tert-butyl, n-pentyl, isopentyl, neopentyl and tert-pentyl radicals, hexyl radicals, such as the n-hexyl radical, heptyl radicals, such as the n-heptyl radical, octyl radicals, such as the 2,2,4-trimethyl radical, and isooctyl radicals, such as the 2,2,4-trimethylpentyl radical, nonyl radicals, such as the n-nonyl radical, decyl radicals, such as the n-decyl radical, dodecyl radicals, such as the n-dodecyl radical, and octadecyl radicals, such as the n-octadecyl radical; alkenyl radicals, such as the vinyl and allyl radicals; cycloalkyl radicals, such as cyclopentyl, cyclohexyl and cycloheptyl radicals, and methylcyclohexyl radicals; aryl radicals, such as the phenyl, naphthyl, anthryl and phenanthryl radicals; alkaryl radicals, such as o-, m- and p-tolyl radicals, xylyl radicals and ethylphenyl radicals; and aralkyl radicals such as the benzyl radical and the α- and β-phenylethyl radicals. Examples of substituted radicals represented by R are cyanoalkyl radicals, such as the β-cyanoethyl radical; halogenated hydrocarbon radicals, for example haloalkyl radicals, such as the 3,3,3-trifluoro-n-propyl radical, the 2,2,2',2',2', -hexafluoroisopropyl radical, the heptafluoroisopropyl radical, and haloaryl radicals, such as the o-, m- and p-chlorophenyl radical: acyloxyalkyl radicals, such as the 3-acetoxypropyl, 3-acryloxypropyl and 3-methacryloxypropyl radicals; alkoxyalkyl radicals, such as the 3-methoxypropyl, 3-(2-methoxyethoxy)propyl and 3-glycidoxypropyl radicals; and mercaptoalkyl radicals, such as the 3-mercaptopropyl and 3-methylthiopropyl radicals.

Examples of radicals represented by $R^2$ are alkyl radicals, such as the methyl, ethyl, n-propyl, isopropyl, 1-n-butyl, 2-n-butyl, isobutyl, tert-butyl, n-pentyl, isopentyl, neopentyl and tert-pentyl radicals, hexyl radicals, such as the n-hexyl radical, heptyl radicals, such as the n-heptyl radical, octyl radicals, such as the n-octyl radical, and isooctyl radicals, such as the 2,2,4-trimethylpentyl radical; alkenyl radicals, such as the vinyl and allyl radicals; cycloalkyl radicals, such as cyclopentyl, cyclohexyl and cycloheptyl radicals, and methylcyclohexyl radicals; aryl radicals, such as the phenyl radical; alkaryl radicals, such as o-, m- and p-tolyl radicals, xylyl radicals and ethylphenyl radicals; and aralkyl radicals, such as the benzyl radical and the α-and β-phenylethyl radicals.

Examples of substituted radicals represented by $R^2$ are halogenated hydrocarbon radicals, such as the 2-chloroethyl and 3-chloropropyl radicals; hydroxyalkyl radicals, such as the 2-hydroxyethyl and 3-hydroxypropyl radicals; alkoxyalkyl radicals, such as the 2-methoxyethyl radical; and aminoalkyl radicals, such as the 2-(dimethylamino)ethyl radical.

An example of the radical represented by $R^3$ is the cyclohexylene radical.

A preferred example of an organodisiloxane (2) is the hexamethyldisiloxane, which is produced as a by-product in the synthesis of antibiotics. Further preferred examples of organodisiloxanes are 1,3-divinyl-1,1,3,3-tetramethyldisiloxane and 1,1,3,3-tetramethyldisiloxane. It is also possible to employ impure organodisiloxanes, for example organodisiloxanes containing solvents such as toluene or chloroform. Amine-containing organodisiloxanes should be neutralized before use.

A particularly preferred example of a chlorosilane of formula (3) is tetrachlorosilane. An example of a chlorosilane containing an Si-bonded organofunctional radical is 3-methacryloxypropyltrichlorosilane.

The reaction occures in accordance with the following reaction schemes:

$$3(R_3SiO)_2O + SiCl_4 \rightarrow ClSi(OSiR_3)_3 + 3R_3SiCl \quad (I)$$

$$3(R_3SiO)_2O + RSiCl_3 \rightarrow RSi(OSiR_3)_3 + 3R_3SiCl \quad (II)$$

$$4(R_3SiO)_2O + SiCl_4 \rightarrow Si(OSiR_3)_4 + 4R_3SiCl \quad (III)$$

At the same time as the preparation of the organosiloxanes (1), triorganochlorosilane is prepared, as shown by the reaction equations (I), (II) and (III).

In the process according to the invention, at least 1 mole of organodisiloxane (2) is preferably employed in the reaction per gram-atom of Si-bonded chlorine in the chlorosilane (3).

Examples of organosiloxanes (1) prepared by the process according to this invention are 3-chloro-3-trimethylsiloxyhexamethyltrisiloxane, 1,1,5,5-tetramethyl3-chloro-3-dimethylsiloxytrisiloxane, 1,5-divinyl-1,1,5,5-tetramethyl-3-chloro-3-vinyldimethylsiloxytrisiloxane, 3-methacryloxypropyl-3-trimethylsiloxyhexamethyltrisiloxane, 3,3-bis-(trimethylsiloxy)hexamethyltrisiloxane, 1,1,5,5-tetramethyl-3,3-bis(dimethylsiloxy)trisiloxane and 1,5,-divinyl-1,1,5,5-tetramethyl-3,3-bis(vinyldimethylsiloxy)trisiloxane.

The phosphonitrile chlorides (4) which catalyze the reaction of organodisiloxanes (2) with chlorosilanes (3) may be, for example, those prepared by reacting 400 parts by weight of phosphorus pentachloride with 130 parts by weight of ammonium-chloride (cf., for example, "Berichte der Deutschen Chemischen Gesellschaft", Volume 57, 1924, p. 1345) or those obtained by reacting 2 moles of phosphorus pentachloride with 1 mole of ammonium chloride (cf., for example, U.S. Pat. No. 3,839,388, to Nitzsche et al.) It is of course also possible to use mixtures of at least two different types of phosphonitrile chlorides.

Phorphonitrile chloride (4) is preferably employed in amounts of from 0.1 to 50 per mil by weight, in particular 0.5 to 20 per mil by weight, based on the total weight of the organosilicon compounds (2) and (3) employed in each case. For better distribution and simpler metering, the phosphonitrile chlorides are employed in the form of their solutions in an inert solvent. Examples of suitable solvents are hydrocarbons, such as hexane or cyclohexane, and halogenated hydrocarbons, such as methylene chloride or 1,2,3-trichloropropane. These solutions preferably contain 20 to 60 percent by weight of phosphonitrile chlorides, based on the total weight of phosphonitrile chlorides and solvent.

Examples of cocatalysts (5) are those of the formulas $HC(O)N(CH_3)_2$, $HC(O)NH_2$, $H_3CC(O)N(CH_3)_2$, $H_3CC(O)NH_2$, $H_2NC(O)NH_2$, $(H_3C)_2NC(O)N(CH_3)_2$, $(n\text{-}Bu)NHC(O)NH(n\text{-}Bu)$,

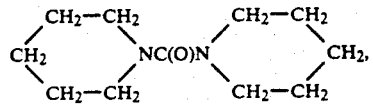

$HO(CH_2)_2NHC(O)NH(CH_2)_2OH$ and $H_3CNHC(O)NHCH_3$.

Preferred examples of cocatalysts (5) are tetramethylurea and N,N'-bis(2-hydroxyethyl)urea.

Cocatalysts (5) are preferably employed in amounts of from 0.1 ppm by weight to 1 percent by weight, and more preferably from 0.1 to 1000 ppm by weight, based on the total weight of the organosilicon compounds (2) and (3) employed in each case. For better distribution and simpler metering, it is also possible to employ the cocatalyst (5) in the form of a solution in an inert solvent, such as a hydrocarbon, for example hexane, or a hydrogenated hydrocarbon, for example methylene chloride.

The process according to the invention is preferably carried out at 0° to 90° C., and more preferably from 20° to 55° C. The pressure used in the process of this invention is usually the pressure of the ambient atmosphere.

The process of this invention is carried out in a simple manner. For example, the organodisiloxane (2) and the chlorosilane (3) are mixed with phosphonitrile chloride (4) and the cocatalyst (5), and the reaction is controlled, preferably with stirring and with temperature control, until the reaction mixture has reacted to completion. The reaction time is preferably from 4 to 100 hours, preferably from 20 to 70 hours.

The catalyst is preferably deactivated after the reaction is complete. This can be accomplished, for example, by removing the reaction products from the catalyst by distillation under reduced pressure or by adsorption of the catalyst onto molecular sieves or by neutralization using bases, such as amines or metal oxides. The deactivation of the catalyst is preferably carried out using tertiary amines or metal oxides. Example of tertiary amines are triethylamine and tri-n-butylamine. An example of a metal oxide is magnesium oxide. Preferably, about 1 to 5 moles of amine or metal oxide are used per gram-atom of phosphorus in the phosphonitrile chlorides. For better distribution and simpler metering, the amines can, for example, be used in the form of their solutions in an inert solvent. These solutions generally contain from 20 to 60 percent by weight of amine, based on the total weight of amine and solvent. The temperature and pressure conditions mentioned for the process of this invention in the reaction of the organodisiloxanes (2) with the chlorosilanes (3) also apply to the neutralization of the catalysts using amines and metal oxides. The organosiloxanes (1) prepared according to the invention are preferably obtained by fractional distillation.

The organosiloxanes (1) prepared according to this invention can be used for all purposes for which organosiloxanes of this type are generally employed. These include, for example, the use as such or as intermediates in the production of moldings and coatings; as crosslinking agents for silicone resins and silicone rubbers; as siloxane chain terminators, as silylating agents for monomers and as protective groups.

The phosphonitrile chloride used in the examples below was prepared in the following manner:

A mixture containing 417 g (2 mol) of phosphorus pentachloride and 53.3 g (1 mol) of ammonium chloride in 1000 ml tetrachloroethane is refluxed for 12 hours. The volatile components are removed at 160° C. at a reduced pressure of about 1.33 hPa (abs.) from the resultant pale yellow solution. The remaining residue consists of yellowish cyrstals comprising essentially a compound of the formula

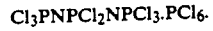

Cl$_3$PNPCl$_2$NPCl$_3$.PCl$_6$.

EXAMPLE 1

About 4.6 g (0.2% by weight) of tetramethylurea and 183.4 g of a 25% solution of phosphonitrile chloride in methylene chloride are added to a mixture containing 1707 g (10.5 mol) of hexamethyldisiloxane and 595 g (3.5 mol) of tetrachlorosilane with stirring in a 4 liter multineck flask fitted with internal thermometer, stirrer and a reflux condenser. The reaction temperature is kept at 45° C. by cooling. After 21 hours, the volatile components of the reaction mixture are removed by distillation at 200 mbar and 100° C. The crude distillate contains 56% of 3-chloro-3-trimethylsiloxyhexamethyltrisiloxane, 29% of 3,3-dichlorohexamethyltrisiloxane and 16% of 3,3-bis(trimethylsiloxy)hexamethyltrisiloxane. The crude distillate is fractionally distilled, and gives, at 20 mbar and 83° to 87° C., 313 g (27% of theory) of 3-chloro-3-trimethylsiloxyhexamethyltrisiloxane in a purity, determined by gas chromatography, of 97%.

COMPARATIVE EXAMPLE 1

About 1.9 ml of a 25% solution of phosphonitrile chloride in methylene chloride are added at room temperature with stirring to a mixture containing 486 g (3.0 mol) of hexamethyldisiloxane and 170 g (1.0 mol) of tetrachlorosilane. After the mixture has been stirred at room temperature for 8 hours, the catalyst is deactivated by adding 2.2 ml of tri-n-butylamine. Distillation of the reaction mixture at 18° to 34° C. and at 2 mbar gives 55 g of 3,3-dichlorohexamethyltrisiloxane, but no 3-chloro-3-trimethylsiloxyhexamethyltrisiloxane. Likewise the desired 3-chloro-3-trimethylsiloxyhexamethyltrisiloxane is neither found in the distillation residue (12 g) nor in the cold trap (583 g of a mixture of trimethylchlorosilane and 1,1,1-trichloro-3,3,3-trimethyldisiloxane).

EXAMPLE 2

About 24 g of a 25% solution of phosphonitrile chloride in methylene chloride are added at room temperature with stirring to a mixture containing 1834 g (9.86 mol) of 1,3-divinyl-1,1,3,3-tetramethyldisiloxane, 2.4 g of 2.5% solution of tetramethylurea in methylene chloride, and 559 g (3.29 mol) of tetrachlorosilane. After 46 hours, the reaction mixture is neutralized using magnesium oxide, and the mixture is filtered. The volatile components of the filtrate are removed by evaporation in a rotary evaporator at 30° C. and at about 4 mbar, and subsequently subjected to fractional distillation. At 93° to 100° C. and at 6 mbar, 334 g (30% of theory) of 1,5-divinyl-1,1,5,5-tetramethyl-3-chloro-3-chloro-3-vinyldimethylsiloxy trisiloxane are obtained in a purity, determined by gas chromatography, of 94%.

COMPARATIVE EXAMPLE 2

About 1 ml of a 25% solution of phosphonitrile chloride in methylene chloride is added to a mixture containing 278 g (1.5 mol) of 1,3-divinyl-1,1,3,3-tetramethyldisiloxane and 85 g (0.5 mol) of tetrachlorosilane. After the mixture has been stirred at room temperature for 116 hours, 1.1 ml of tri-n-butylamine are added, and the reaction mixture stirred for an additional 30 minutes and then subsequently fractionally distilled. At 45° to 52° C. and at 3 mbar, 85 g of 1,5-divinyl-1,1,5,5-tetramethyl-3,3-dichlorotrisiloxane are obtained, but no 1,5-divinyl-1,1,5,5-tetramethyl-3-chloro-3-vinyldimethylsiloxytrisiloxane.

EXAMPLE 3

A mixture containing 972 g (6.0 mol) of hexamethyldisiloxane, 261 g (1.0 mol) of 3-methacryloxypropyltrichlorosilane, 9.86 g of a 25% solution of phosphonitrile chloride in methylene chloride, 0.24 g of tetramethylurea and 0.3 g of 2,6-di-tert-butyl-4-methylphenol is stirred at room temperature for 70 hours. Trichlorosilane and excess hexamethyldisiloxane are then removed by evaporation, the residue is washed with water until neutral, dried using sodium sulfate and filtered. The filtrate is then fractionally distilled via a distillation column. As the principal fraction, 215 g (51% of theory) of 3-methacryloxypropyl-3-trimethylsiloxyhexamethyltrisiloxane are obtained at 110° to 115° C. and at 5 mbar with a purity, determined by gas chromatography, of 99.7%.

COMPARATIVE EXAMPLE 3

A mixture containing 243 g (1.5 mol) of hexamethyldisiloxane, 65.4 g (0.25 mol) of 3-methacryloxypropyltrichlorosilane, 900 ppm of phosphonitrile chloride and 500 ppm of 2,6-di-tert-butyl-4-methylphenol is stirred at room temperature for 116 hours. The phosphonitrile chloride is deactivated by adding 0.96 ml of tri-n-butylamine, and the reaction mixture is subsequently fractionally distilled. About 25 g (23% of theory) of 3-methacryloxypropyl-3-trimethylsiloxyhexamethyltrisiloxane are obtained at 107° to 113° C. and at 3 mbar.

EXAMPLE 4

About 22.8 ml of a 25% solution of phosphonitrile chloride in 1,2,3-trichloropropane are added at room temperature with stirring to a mixture containing 243 g (1.5 mol) of hexamethyldisiloxane, 42.5 g (0.25 mol) of tetrachlorosilane and 0.35 g of N,N'-bis(2-hydroxyethyl)urea. After 21 hours, excess hexamethyldisiloxane and trimethylchlorosilane are removed by distillation at 30° C. and at 20 mbar. About 50 ml of water are added to the residue, the water phase is subsequently removed, and the organic phase is dried using sodium sulfate and then subsequently fractionally distilled. About 75 g (78% of theory) of 3,3-bis(trimethylsiloxy)hexamethyltrisiloxane are obtained at 35° to 47° C. and at 3 mbar.

EXAMPLE 5

A mixture containing 85 g (0.5 mol) of tetrachlorosilane and 186 g (1.0 mol) of 1,3-divinyl-1,1,3,3-tetramethyldisiloxane are added dropwise over a period of 6 hours at 25° C. to a mixture containing 558 g (3.0 mol) of 1,3-divinyl-1,1,3,3-tetramethyldisiloxane, 0.32 g of tetramethylurea and 12.9 g of a 25% solution of phosphonitrile chloride in methylene chloride. After an additional reaction time of 20 hours, the volatile components are removed from the reaction mixture by distillation at 30° C. and at 20 mbar. The residue is filtered off via 50 g of silica gel, and the filtrate is then subjected to fractional distillation. About 85 g (44% of theory) of 1,5-divinyl-1,1,5,5-tetramethyl-3,3-bis-(vinyldimethylsiloxy)trisiloxane are obtained at 85° to 105° C. and at 2 mbar.

COMPARATIVE EXAMPLE 5

A mixture containing 595 g (3.2 mol) of 1,3-divinyl-1,1,3,3-tetramethyldisiloxane, 136 g (0.8 mol) of tetrachlorosilane and 2 ml of a 25% solution of phosphonitrile chloride in methylene chloride is stirred at room temperature for 8 hours. About 2.3 ml of tri-n-butylamine are then added to deactivate the phosphonitrile chloride. The reaction mixture is stirred for 30 minutes and then subjected to fractional distillation. About 216 g of 1,1,1-trichloro-3-vinyl-3,3-dimethyldisiloxane are obtained at 20° to 22° C. at 2 mbar; about 53 g of 1,5-divinyl1,1,5,5-tetramethyl 3,3-dichlorotrisiloxane are obtained at 23° to 42° C. and at 2 mbar, and 9 g of a 1:1 mixture of 1,5divinyl-1,1,5,5-tetramethyl-3,3-dichlorotrisiloxane and 1,5-divinyl-1,1,5,5-tetramethyl-3-chloro-3-trimethylsiloxytrisiloxane are obtained at 42° to 72° C. and at 2 mbar. About 372 g of vinyldimethylchlorosilane are collected in the cold trap. The desired 1,5-divinyl-1,1,5,5-tetramethyl-3,3-bis(vinyldimethylsiloxy)trisiloxane is not obtained.

EXAMPLE 6

A mixture containing 804 g (6.0 mol) of tetramethyldisiloxane, 1740 g (1.0 mol) of tetrachlorosilane, 0.2 g of tetramethylurea and 7.8 g of a 25% solution of phosphonitrile chloride in methylene chloride is stirred at room temperature for 28 hours. The readily volatile components are then removed by evaporation at 20° C. and at 20 mbar, and the residue is washed with water until neutral, dried using sodium sulfate and subjected to fractional distillation via a Vigreux column. About 135.2 g (41% of theory) of 1,1,5,5-tetramethyl-3,3-bis(-dimethylsiloxy)trisiloxane are obtained at 47° to 60° C. and at 2 mbar.

COMPARATIVE EXAMPLE 6

A mixture containing 536 g (4.0 mol) of tetramethyldisiloxane, 170 g (1.0 mol) of tetrachlorosilane and 2 ml of a 25% solution of phosphonitrile chloride in methylene chloride is stirred at room temperature for 116 hours. About 1.1 ml of tri-n-butylamine are then added to deactivate the phosphonitrile chloride. The reaction mixture is stirred for 30 minutes and then subjected to fraction distillation. About 17 g of 1,1,5,5-tetramethyl-3,3-dichlorotrisiloxane are obtained at 30° to 43° C. and at 10 mbar, and 98 g of 1,1,5,5-tetra methyl-3-chloro-3-dimethylsiloxytrisiloxane are obtained at 44° to 47° C. and at 10 mbar, but the desired 1,1,5,5-tetramethyl-3,3-bis(dimethylsiloxy)trisiloxane is not obtained.

COMPARATIVE EXAMPLE 7

About 0.04 g of $FeCl_3$ are added to a mixture containing 2.68 g (2.0 mol) of tetramethyldisiloxane and 85 g (0.5 mol) of tetrachlorosilane, and HCl is subsequently introduced for 2 minutes. During this operation, the temperature of the mixture increases to 40° C. The reaction mixture is stirred for an additional 4 hours and then subjected to fractional distillation via a Vigreux column. About 41 g of a mixture of 1,1,5,5-tetramethyl-3,3-dichlorotrisiloxane and tetramethyldisiloxane are obtained at 20° to 46° C. and at 1 mbar, and 13.5 g of 1,1,5,5-tetramethyl-3-chloro-3-dimethylsiloxytrisiloxane are obtained at 46° to 48° C. and at 1 mbar. The desired 1,1,5,5-tetramethyl-3,3-bis(dimethylsiloxy)trisiloxane is not obtained.

What is claimed is:

1. A process for preparing organosiloxanes (1) of the general formula $$R_{4-n}{}^1Si(OSiR_3)_n,$$

in which R is selected from the group consisting of a hydrogen atom, a monovalent hydrocarbon radical having from 1 to 18 carbon atoms per radical and a substituted monovalent hydrocarbon radical having from 1 to 18 carbon atom per radical, R1 is selected from the group consisting of R and a chlorine atom, and n is 3 or 4, which comprises reacting an organodisiloxane (2) of the general formula $$(R_3Si)_2O,$$

with a chlorosilane (3) of the general formula $$R_{4-n}SiCl_n,$$

in which R and n are the same as above, in the presence of phosphonitrile chlorides (4) and a cocatalyst (5), in which the cocatalyst (5) is used concomitantly with the phosphonitrile chlorides (4) and is selected from the group consisting of amides of the general formula $$X\text{-}C(O)\text{-}R^2,$$

in which $R^2$ is selected from the group consisting of a hydrogen atom, a monovalent hydrocarbon radical having from 1 to 8 carbon atoms per radical and a substituted monovalent hydrocarbon radical having from 1 to 8 carbon atom per radical, and X is selected from th consisting of a radical of the formula $R^2{}_2N$- and $$\boxed{R^3N\text{—}},$$

where $R^2$ is the same as above and $R^3$ is a divalent hydrocarbon radical having from 5 to 7 carbon atoms per radical, urea, urea derivatives of the general formula $$X\text{-}C(O)\text{-}X,$$

where X is the same as above and cyanuric acid.

2. The process of claim 1, wherein the phosphonitrile chlorides (4) are deactivated when the reaction is complete.

3. The process of claim 1, wherein the cocatalyst (5) is used in an amount of from 0.1 ppm by weight to 1 percent by weight, based on the total weight of the organosilicon compounds (2) and (3).

4. The process of claim 2, wherein the cocatalyst (5) is used in an amount of from 0.1 ppm by weight to 1 percent by weight, based on the total weight of the organosilicon compounds (2) and (3).

5. The process of claim 1, wherein the phosphonitrile chlorides (4) are used in an amount of from 0.1 to 50 per mil by weight and the cocatalyst (5) is used in an amount of from 0.1 ppm to 1 percent by weight based on the total weight of the organosilicon compounds (2) and (3).

6. The process of claim 1, wherein cocatalyst (5) is an amide of the formula

X-C(O)-R$^2$, where R$^2$ is selected from the group consisting of a hydrogen atom, a monovalent hydrocarbon radical having from 1 to 8 carbon atoms per radical and a substituted monovalent hydrocarbon radical having from 1 to 8 carbon atoms per radical, and X is selected from the group consisting of a radical of the formula R$^2{}_2$N- and

R$^2$ is selected from the group consisting of hydrogen atom, a monovalent hydrocarbon radical having from 1 to 8 carbon atoms per radical and a substituted monovalent hydrocarbon radical having from 1 to 8 carbon atoms per radical and R$^3$ is a divalent hydrocarbon radical having from 5 to 7 carbon atoms per radical.

7. The process of claim 1, wherein the cocatalyst (5) is a urea derivative of the formula

X-C(O)-X, where X is selected from the group consisting of a radical of the formula R$^2{}_2$N- and

R$^3$N—,

R$^2$ is selected from the group consisting of a hydrogen atom, a monovalent hydrocarbon radical having from 1 to 8 carbon atoms per radical and a substituted monovalent hydrocarbon radical having from 1 to 8 carbon atoms per radical and R$^3$ is a divalent hydrocarbon radical having from 5 to 7 carbon atoms per radical.

8. The process of claim 1, wherein the cocatalyst (5) is urea.

9. The process of claim 1, wherein the cocatalyst (5) is cyanuric acid.

* * * * *

UNITED STATES PATENT AND TRADEMARK OFFICE
CERTIFICATE OF CORRECTION

PATENT NO. : 5,011,962
DATED : April 30, 1991
INVENTOR(S) : Gerhard Staiger, Johann Müller and Walter Doskocil It is certified that error appears in the above-identified patent and that said Letters Patent is hereby corrected as shown below:

column 1, under "Inventors", after Staiger delete "Altölling" and insert ---Altötting---.

Signed and Sealed this

Ninth Day of February, 1993

Attest:

STEPHEN G. KUNIN

*Attesting Officer*      Acting Commissioner of Patents and Trademarks